(12) United States Patent
Moffitt et al.

(10) Patent No.: US 8,423,157 B2
(45) Date of Patent: *Apr. 16, 2013

(54) ELECTRODE CONTACT CONFIGURATIONS FOR CUFF LEADS

(75) Inventors: Michael Adam Moffitt, Valencia, CA (US); Rafael Carbunaru, Studio City, CA (US); Kristen N. Jaax, Saugus, CA (US); Todd K. Whitehurst, Santa Clarita, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 64 days.

This patent is subject to a terminal disclaimer.

(21) Appl. No.: 13/114,898

(22) Filed: May 24, 2011

(65) Prior Publication Data
US 2011/0224744 A1 Sep. 15, 2011

Related U.S. Application Data

(63) Continuation of application No. 11/393,991, filed on Mar. 30, 2006, now Pat. No. 7,974,706.

(51) Int. Cl.
*A61N 1/05* (2006.01)
*A61N 1/18* (2006.01)
*A61N 1/04* (2006.01)

(52) U.S. Cl.
USPC .............................. 607/118; 600/377; 607/45

(58) Field of Classification Search .................... 607/45, 607/118, 2
See application file for complete search history.

(56) References Cited

U.S. PATENT DOCUMENTS

| 3,941,136 A | 3/1976 | Bucalo |
| 4,033,357 A | 7/1977 | Helland et al. |
| 4,135,518 A | 1/1979 | Dutcher |
| 4,301,815 A | 11/1981 | Doring |
| 4,542,753 A | 9/1985 | Brenman et al. |
| 4,585,005 A | 4/1986 | Lue et al. |

(Continued)

FOREIGN PATENT DOCUMENTS

| WO | 98/37926 | 9/1998 |
| WO | 98/43700 | 10/1998 |
| WO | 98/43701 | 10/1998 |

OTHER PUBLICATIONS

Rattay, F., "Analysis of Models for External Stimulation of Axons," IEEE Transactions on Biomedical Engineering, BME-33 (10):974-977, 1986.

(Continued)

*Primary Examiner* — Carl H Layno
*Assistant Examiner* — Jon Eric C Morales
(74) *Attorney, Agent, or Firm* — Frommer Lawrence & Haug LLP; Bruce E. Black

(57) ABSTRACT

A stimulation system is disclosed that may include a stimulator unit coupled to electrode contacts on a cuff. In one embodiment, the cuff may be placed at least partially around a nerve. The stimulation system may include at least two electrode contacts disposed on the cuff such that a distance between the at least two electrode contacts various along a length of the electrode contacts. In another embodiment, a plurality of electrode contacts are disposed on the cuff such that distances between at least one electrode contact within the plurality of electrode contacts and each electrode contact immediately adjacent to the at least one electrode contact are different. The stimulator unit may also be implantable.

19 Claims, 8 Drawing Sheets

U.S. PATENT DOCUMENTS

| | | | |
|---|---|---|---|
| 4,702,254 | A | 10/1987 | Zabara |
| 4,722,353 | A | 2/1988 | Sluetz |
| 4,796,643 | A | 1/1989 | Nakazawa et al. |
| 4,867,164 | A | 9/1989 | Zabara |
| 4,920,979 | A * | 5/1990 | Bullara .................. 607/118 |
| 4,934,368 | A | 6/1990 | Lynch |
| 4,957,118 | A | 9/1990 | Erlebacher |
| 5,025,807 | A | 6/1991 | Zabara |
| 5,193,539 | A | 3/1993 | Schulman et al. |
| 5,193,540 | A | 3/1993 | Schulman et al. |
| 5,251,634 | A * | 10/1993 | Weinberg .................. 600/377 |
| 5,312,439 | A | 5/1994 | Loeb |
| 5,314,457 | A | 5/1994 | Jeutter et al. |
| 5,324,322 | A | 6/1994 | Grill et al. |
| 5,376,108 | A | 12/1994 | Collins et al. |
| 5,433,735 | A | 7/1995 | Zanakis et al. |
| 5,439,938 | A | 8/1995 | Synder et al. |
| 5,454,840 | A | 10/1995 | Krakovsky et al. |
| 5,571,118 | A | 11/1996 | Boutos |
| 5,741,319 | A | 4/1998 | Woloszko et al. |
| 5,775,331 | A | 7/1998 | Raymond et al. |
| 5,938,584 | A | 8/1999 | Ardito et al. |
| 6,051,017 | A | 4/2000 | Loeb et al. |
| 6,058,332 | A | 5/2000 | Dahl |
| 6,181,969 | B1 | 1/2001 | Gord |
| 6,188,932 | B1 | 2/2001 | Lindegren |
| 6,308,105 | B1 * | 10/2001 | Duysens et al. .............. 607/118 |
| 6,516,227 | B1 | 2/2003 | Meadows et al. |
| 6,609,029 | B1 | 8/2003 | Mann et al. |
| 6,609,032 | B1 | 8/2003 | Woods et al. |
| 6,650,943 | B1 | 11/2003 | Whitehurst et al. |
| 6,735,474 | B1 | 5/2004 | Loeb et al. |
| 6,741,892 | B1 | 5/2004 | Meadows et al. |
| 6,788,975 | B1 | 9/2004 | Whitehurst et al. |
| 7,003,352 | B1 | 2/2006 | Whitehurst |
| 7,006,875 | B1 | 2/2006 | Kuzma et al. |
| 7,584,004 | B2 | 9/2009 | Caparso et al. |
| 7,596,414 | B2 | 9/2009 | Whitehurst et al. |
| 7,610,103 | B2 | 10/2009 | Whitehurst et al. |
| 7,706,892 | B2 | 4/2010 | Colvin et al. |
| 7,761,165 | B1 | 7/2010 | He et al. |
| 7,840,279 | B2 | 11/2010 | He |
| 7,953,498 | B1 | 5/2011 | Carbunaru et al. |
| 7,974,706 | B2 * | 7/2011 | Moffitt et al. .................. 607/118 |
| 2003/0236558 | A1 * | 12/2003 | Whitehurst et al. ............ 607/45 |
| 2004/0010303 | A1 * | 1/2004 | Bolea et al. .................... 607/118 |
| 2004/0059392 | A1 | 3/2004 | Parramon et al. |
| 2004/0111139 | A1 | 6/2004 | McCreery |
| 2005/0010265 | A1 | 1/2005 | Baru Fassio et al. |
| 2006/0282145 | A1 * | 12/2006 | Caparso et al. ............... 607/118 |

OTHER PUBLICATIONS

European Search Report for European Patent Application 07717567.7 mailed Jun. 1, 2011.

International Search Report and Written Opinion for International Patent Application No. PCT/US2007/061660 mailed Oct. 3, 2007.

International Preliminary Report on Patentability for International Patent Application No. PCT/US2007/061660 mailed Oct. 9, 2008.

Office Communication for U.S. Appl. No. 11/393,991 mailed Jan. 21, 2009.

Office Communication for U.S. Appl. No. 11/393,991 mailed Jun. 25, 2009.

Office Communication for U.S. Appl. No. 11/393,991 mailed Sep. 8, 2009.

Office Communication for U.S. Appl. No. 11/393,991 mailed Feb. 17, 2010.

Office Communication for U.S. Appl. No. 11/393,991 mailed May 20, 2010.

Office Communication for U.S. Appl. No. 11/393,991 mailed Sep. 3, 2010.

Office Communication for U.S. Appl. No. 11/393,991 mailed Dec. 22, 2010.

Office Communication for U.S. Appl. No. 11/393,991 mailed Mar. 3, 2011.

* cited by examiner

US 8,423,157 B2

ELECTRODE CONTACT CONFIGURATIONS FOR CUFF LEADS

CROSS-REFERENCE TO RELATED APPLICATIONS

This patent application is a continuation of U.S. patent application Ser. No. 11/393,991 filed on Mar. 30, 2006, now U.S. Pat. No. 7,974,706 which is incorporated herein by reference.

FIELD OF THE INVENTION

The invention relates generally to electrode contacts for neurostimulation, and more particularly, but not exclusively, to devices with asymmetric (different) electrode contact configurations for peripheral nerve stimulation, stimulation of nerve bundles, neurovascular bundles, and subcutaneous stimulation and methods of manufacture and use.

BACKGROUND OF THE INVENTION

Neurostimulation is the application of electrical stimulation on neurological pathways, such as nerve bundles, neurovascular bundles, and so forth. Electrical stimulation has a history in medicine for treating various ailments. For example, neurostimulation has been used for the treatment of chronic radiculopathy (sciatica), failed back syndrome, neuropathy, reflex sympathetic dystrophy (complex regional pain syndrome), and various vascular insufficiencies.

In addition, vagus nerve stimulation (VNS) has been applied with partial success in patients with refractory epilepsy. In this procedure, an implantable pulse generator is implanted in the patient's thorax, and an electrode lead is routed from the generator to the left vagus nerve in the neck. Helix-shaped stimulation and indifferent electrode contacts are attached to the vagus nerve via an invasive surgical process that requires the carotid sheath to be fully exposed. Based on a number of studies, approximately 5% of patients undergoing VNS are seizure-free, and an additional 30-40% of patients have a greater than 50% reduction in seizure frequency. However, VNS may lead to significant side effects. The vagus nerve provides parasympathetic innervation to the cardiac tissue, and thus VNS may lead to bradycardia, arrhythmia, or even graver cardiac side effects. In fact, VNS systems are often only used on the left vagus nerve, as the right vagus nerve contributes significantly to cardiac innervation. Additionally, VNS may interfere with proper opening of the vocal cords, which has led to hoarseness and shortness of breath in a significant number of VNS patients.

Electrical stimulation has also been used to treat erectile dysfunction. The targets of electrical stimulation are the cavernous nerves. The cavernous nerves run bilaterally between the prostate and the rectum as they course from the sacral spinal cord to the corpora cavernosa in the penis. Near the rectum the nerves form more of a plexus than a coherent nerve, and they are interlaced with small arteries and veins as well as fatty tissue. This collection of small nerve fibers, arteries, and veins can be referred to as the neurovascular bundle.

BRIEF SUMMARY

One embodiment is a stimulation system for a nerve. The stimulation system includes a cuff for placement, at least partially, around the nerve, and a plurality of electrode contacts disposed on the cuff. The electrode contacts are disposed such that distances between at least one electrode contact and each electrode contact immediately adjacent to the at least one electrode contact are different. The stimulation system may also include a stimulator unit coupled to the electrode contacts of the cuff. The stimulator unit may also be implantable.

Another embodiment is another stimulation system for a nerve. The stimulation system includes a cuff that is configured and arranged to be disposed over at least a portion of the nerve. At least two electrode contacts are disposed on the cuff such that a distance between the at least two electrode contacts varies along a length of at least one of the electrode contacts. The stimulation system may also include a stimulator unit coupled to the electrode contacts of the cuff. The stimulator unit may also be implantable.

Yet another embodiment is a method of stimulating a nerve by disposing a cuff around the nerve. A plurality of electrode contacts is disposed on the cuff such that distances between at least one electrode contact within the plurality of electrode contacts and each electrode contact immediately adjacent to the at least one electrode contact are different. The cuff is coupled to a stimulator unit and electrical signals are provided from the stimulator unit to the electrode contacts of the cuff to stimulate the nerve.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

Figure 1:
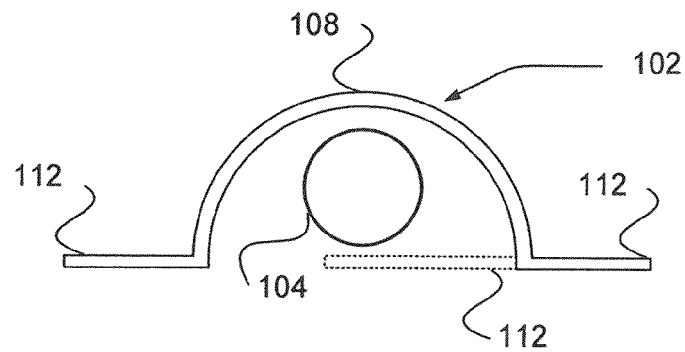
FIG. 1 is a schematic cross-sectional view of one embodiment of a cuff for use in a stimulation system.

The invention is directed to positioning of electrode contacts, as well as devices that include the electrode contacts, for nerve stimulation and treatment of disorders. In addition, the invention is directed to implantable stimulation systems with electrode contacts positioned on a cuff arrangement and for the treatment of disorders. For example, the implantable stimulation systems can be used to stimulate the vagus nerve to treat epilepsy or other disorders or to stimulate the cavernous nerve to treat erectile dysfunction or other disorders. Stimulation of the vagus or cavernous nerve is described herein as examples of use of the inventive implantable stimulation systems; however, it will be recognized that the implantable stimulation systems and components that are disclosed herein can be used to stimulate other nerves and tissues.

Electrode contact arrays can be disposed near or adjacent a nerve to stimulate the nerve, such as, for example, the left vagus nerve or the cavernous nerve. In some instances, however, it is more convenient and/or advantageous to implant a stimulator unit, such as a stimulator, elsewhere, and then couple the stimulator unit, via a conductor, to electrode contacts disposed around or near the nerve. For example, implanting the stimulator unit elsewhere may be desirable so that the stimulator unit is not disposed in the highly mobile neck or groin region where the stimulator unit might be dislodged or otherwise moved from the original implanted position. In addition or alternatively, the stimulator unit may be implanted elsewhere to provide an easier site for removal of the stimulator unit if it should malfunction, cease functioning, or otherwise require replacement or removal. Finally, the stimulator unit may be implanted at a site where a rechargeable battery, if present, can be easily and/or inconspicuously recharged.

Examples of suitable implantable stimulator devices, including stimulators, that can be used or modified for use in stimulating the nerve include, but are not limited to, stimulator devices described in U.S. patent application Ser. No. 11/294,283 entitled "Cuff Electrode Arrangement For Nerve Stimulation And Methods Of Treating Disorders," which is incorporated herein by reference.

Positioning of electrode contacts on a cuff, saddle, or paddle may be selected to reduce stimulation thresholds for nerves and tissues. The positioning of the electrode contacts can be based, in part, on an electrode contact to target nerve or tissue distance. This positioning selection of electrode contacts can be directed towards affording flexibility in a choice of electrode contact spacing, and may be employed to reduce or minimize a stimulation threshold for nerve or tissue at different distances from the electrode contacts. The positioning selection may further afford improved depth selectivity in at least some embodiments. A flexible electrode contact positioning allows electrode contact spacing to be modified (including post-implant) to match or approximate optimal spacings determined empirically or predicted with a theoretical and/or empirical model.

Figure 2:
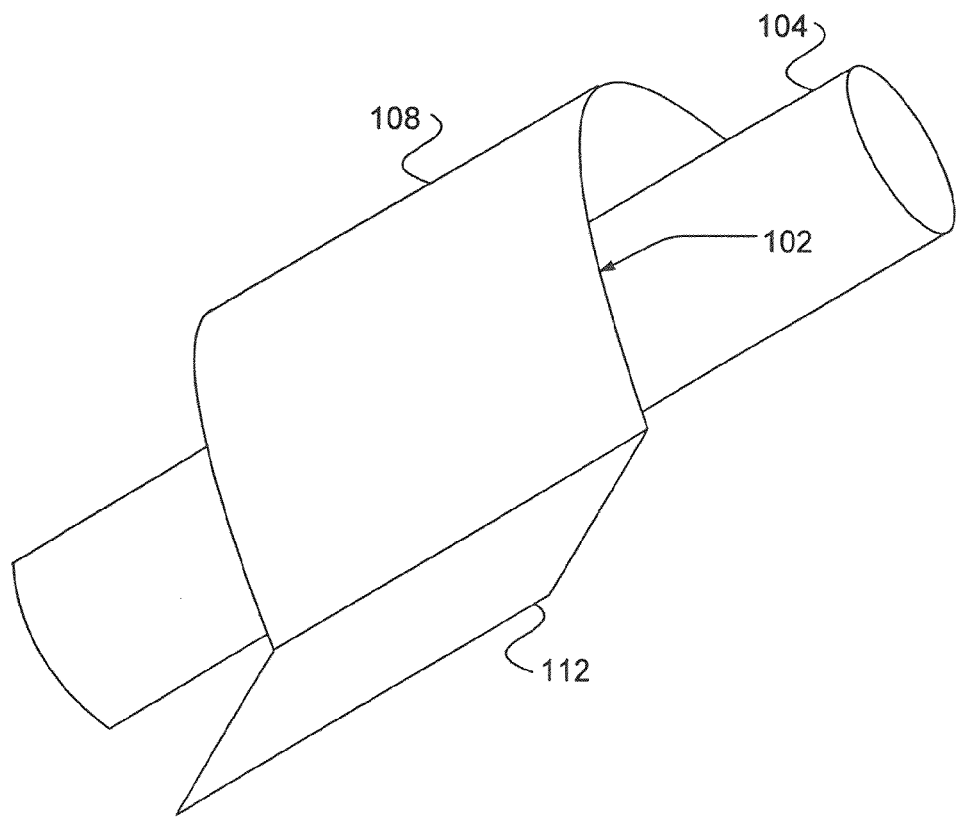
FIG. 2 is a schematic angled side view of one embodiment of a portion of the cuff of FIG. 1.

FIG. 1 shows a cross-sectional view of one embodiment of a cuff for use with a separate stimulator unit. As shown in the figure, in one embodiment, cuff 102 includes a first portion 108 and optional second portions 112. In one embodiment, first portion 108 may be curved. However, the invention is not so limited, and first portion 108 may also be relatively flat. In one embodiment, second portions 112 are relatively flat. Cuff 102 is disposed around the nerve 104. FIG. 2 is an angled side view of one embodiment of a portion of the cuff 102 of FIG. 1 around at least a portion of nerve 104.

The cuff 102 can be formed to curve around most or all of the nerve, or the cuff 102 can be formed with first portion 108 that is disposed around a first portion of the nerve 104 and second portions 112 that may be disposed around a second portion of the nerve 104. For example, at least some of the second portions 112 of the cuff 102 can be positioned between the cavernous nerve and the rectum to facilitate stimulation of the cavernous nerve to treat erectile dysfunction or other disorders. Placing the cuff around all or most of the nerve (or neurovascular bundle) can facilitate recruitment of more of the nerve tissue for stimulation.

The cuff 102 includes two or more electrode contacts that are coupled to a stimulator unit and provides electrical stimulation to the selected nerve, via a conductor 1450 as described in more detail below in conjunction with FIG. 14. Cuff 102 with electrode contacts may be referred to an electrode; while a lead may refer to the electrode combined with conductor 1450.

The electrode contacts can be positioned on the first portion 108 of the cuff 102. Positioning of the electrode contacts is described in more detail below in conjunction with FIGS. 3-12. The cuff 102 typically includes one or more anodes and one or more cathodes. The number of anodes and cathodes may be the same or different. The definition of which electrode contacts are anodes and which are cathodes may be constant or can be altered by the stimulator unit during operation of the stimulator device. When multiple anodes (or cathodes) are used, the anodes (or cathodes), or a subset thereof, can be electrically connected to each other at the cuff or the conductor or they may be each independently connected to the stimulator unit. Independent control of each electrode contact can be particularly useful for steering the current produced by the cuff to provide selective stimulation of desired portions (e.g., bundles of axons) of the nerve.

The electrode contacts are formed of a conductive material. Preferably, the electrode contacts are formed of a material that does not substantially corrode under the operating conditions and in the operating environment for the expected lifetime of the stimulator device. Examples of suitable materials include metals, alloys, conductive plastics, and other conductive materials such as, for example, titanium, iridium, platinum, platinum iridium, stainless steel, or the like.

The electrode contacts can be formed entirely of a single conductive material, such as a metal or alloy, or one or both of the electrode contacts can be formed using a combination of conductive materials such as, for example, a conductive coating over a bulk metallic electrode. In other embodiments, one or both of the electrode contacts can be formed from a polymeric material that is at least partially, or fully, coated with a conductive coating, such as a metal, alloy, or conductive oxide (e.g., iridium tin oxide) coating.

The cuff 102 can be formed using a plastic or cloth material with conductors disposed in or on the material and coupled between the electrode contacts and the conductor. The cuff 102 may also be formed of other materials including silicone, polymers, or the like. The cuff 102 should be biocompatible and preferably does not substantially degrade during the expected implanted period. The cuff 102 can be formed using any method including, for example, molding. The electrode contacts can be coupled to the cuff 102 by any method including molding the cuff 102 around the electrode contacts that go to the conductor 1450 (See FIG. 14) or by attaching the electrode contacts to the cuff 102 by adhesive or other attachment methods.

Figure 3:
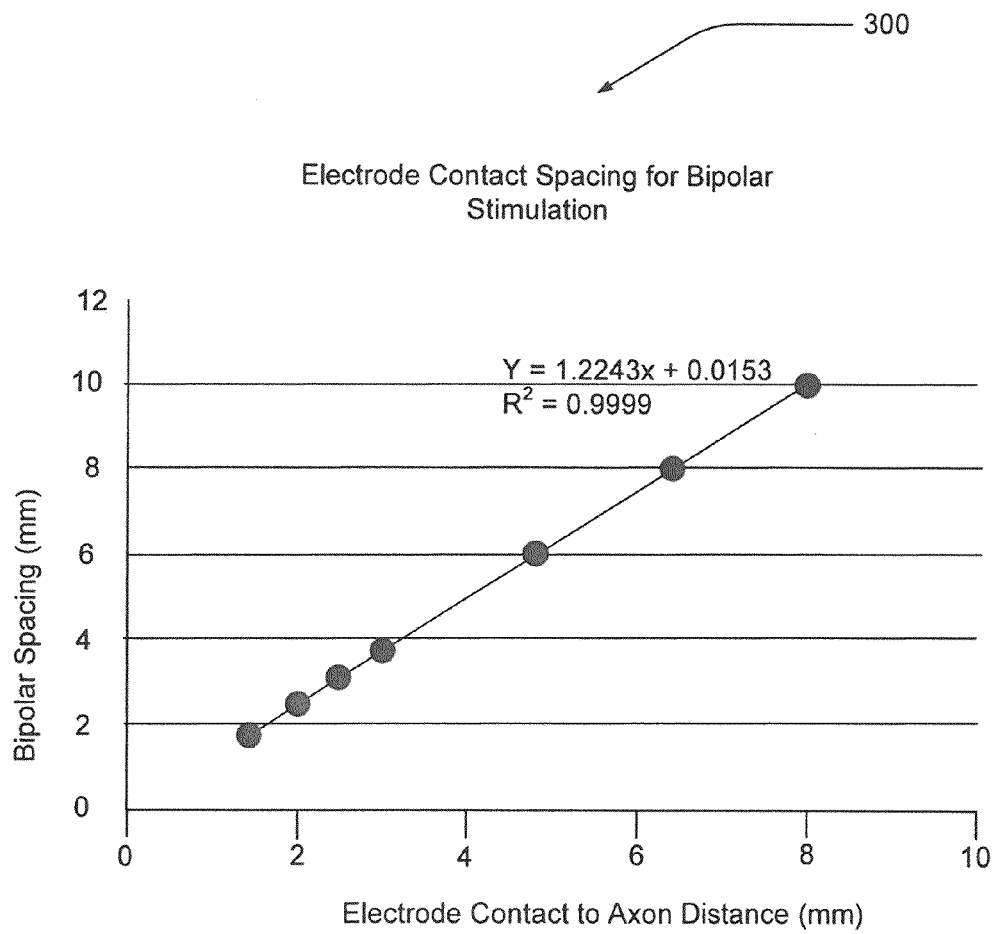
FIG. 3 is a graph illustrating one embodiment of electrode contact spacing for bipolar nerve stimulation.

FIG. 3 is a graph illustrating one embodiment of optimal electrode contact spacing for bipolar nerve stimulation. Positioning of the electrode contacts on the cuff 102 may be selected to reduce stimulation thresholds of the nerve or other fiber. Electrode contacts are positioned in a flexible arrangement such that electrode contacts may be selected to reduce stimulation thresholds and to improve depth selectivity. As shown in FIG. 3, distances between electrode contacts may be determined based on a distance from an axon (e.g., a stimulation target). In one embodiment, a distance between electrode contacts may be based on a shortest distance between a point on one electrode contact and a point on another electrode contact. The distances or spacing between electrode contacts shown in the figure are derived from a theoretical model of stimulation of unmyelinated fibers. However, distances between electrode contacts may also be selected based on other types of fibers, without departing from the scope or spirit of the invention. Moreover, in one embodiment, a theoretical model, similar to that shown in FIG. 3, may be developed based, in part, on a point source within an isotropic homogenous medium of about 500 Ohm-cm using an activating function concept. (See, e.g., Rattay F, "Analysis of Models for External Stimulation of Axons," IEEE Transactions on Biomedical Engineering, Vol. BME-33, No. 10, October 1986, incorporated herein by reference.)

As used in practice, several electrode contacts may be positioned on cuff 102 of FIG. 1 with the separation between adjacent electrode contacts being selected to range around a particular distance. The distance may be a theoretical distance or an experimental distance. For example, given an electrode contact to axon distance of 6 mm, graph 300 of FIG. 3 indicates that a distance between electrode contacts might be 7.3611 mm. However, in practice the electrode contact to axon distance might not actually be 6 mm, due to variety of reasons. Thus, electrode contacts on the cuff 102 could be placed such that distances between any two electrode contacts vary around the theoretical 7.3611 mm. For example, in one embodiment, electrode contacts may be positioned such that distances between at least one electrode contact and each electrode contact immediately adjacent to the at least one electrode contact are different. For this example, a distance between a center electrode contact and an electrode contact adjacent to the center electrode contact might be 7.3611 mm plus some value, while a distance between the center electrode contact and another adjacent electrode contact might be 7.3611 mm minus a different value. However, the invention is not so limited, and other arrangements may also be selected. In this manner, there is flexibility in the selection of different electrode contact based on the variability between theoretical models and empirical observations. FIGS. 4-7, and 11-12 provide various embodiments for positioning of a plurality of electrode contacts on the cuff.

Figure 4:
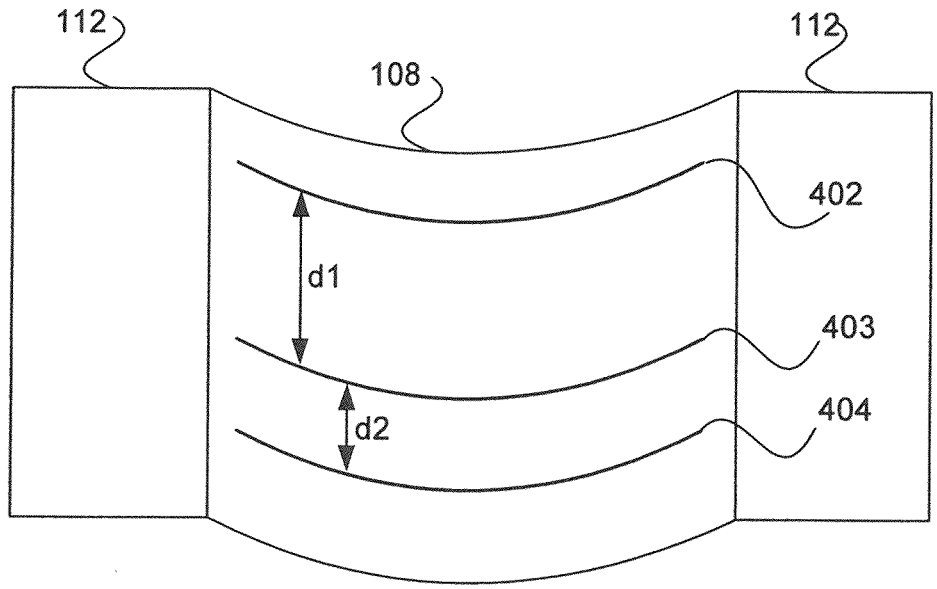
FIG. 4 is a schematic view of an embodiment of a portion a cuff showing positioning of electrode contacts.

FIG. 4 is a schematic view of an embodiment of a portion a cuff showing positioning of electrode contacts. As shown in the figure, three electrode contacts (402-404) are positioned along the first portion 108 of the cuff. The electrode contacts 402-404 may be positioned such that the distances between the center electrode contact 403 and the other two adjacent electrode contacts (402 and 404) are different. That is distance d1 is different from distance d2. In this manner, three bipolar distances are possible for stimulation (e.g., d1, d2, and d1+d2) depending upon the selection of electrode contacts.

Figure 5:
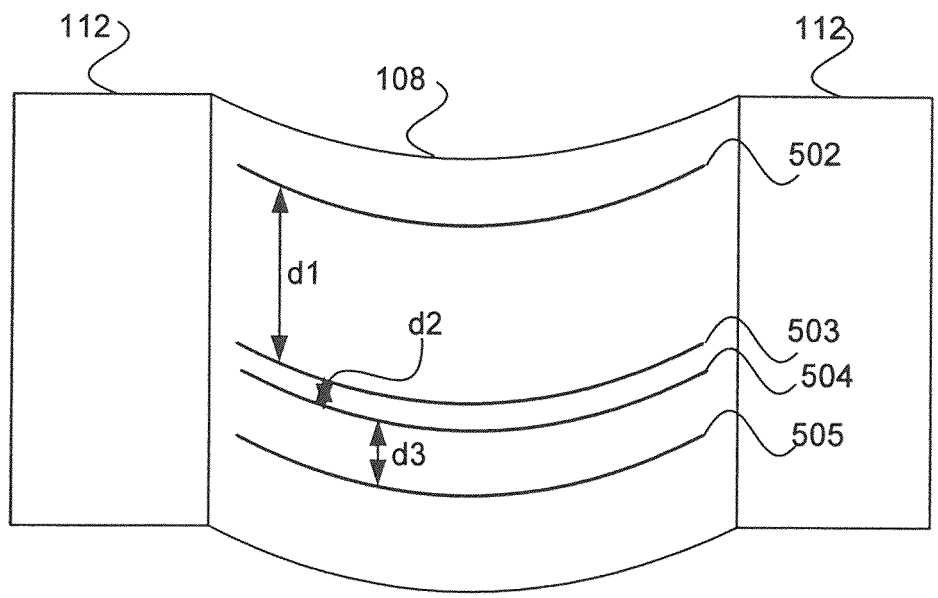
FIG. 5 is a schematic view of another embodiment of a cuff showing another positioning of electrode contacts.

FIG. 5 is a schematic view of another embodiment of a cuff showing another positioning of electrode contacts. As shown in the figure, four electrode contacts 502-55 are positioned such that the distances d1, d2, and d3 are different. In this embodiment, distances d1, d2, and d3 may be selected such that distances d1+d2, d1+d3, d2+d3, and d1+d2+d3 are each different. This enables seven different bipolar distances to be achieved. It will be understood that the invention is not limited to three or four electrode contact arrangements, and similar arrangements can also be made using virtually any number of electrode contacts greater than two.

It should be noted, however, that some embodiments may include repeated distances. However, electrode contacts are spaced such that two or more bipolar (e.g., multipolar) distances can be achieved through asymmetric (different) electrode contact positioning.

Figure 6:
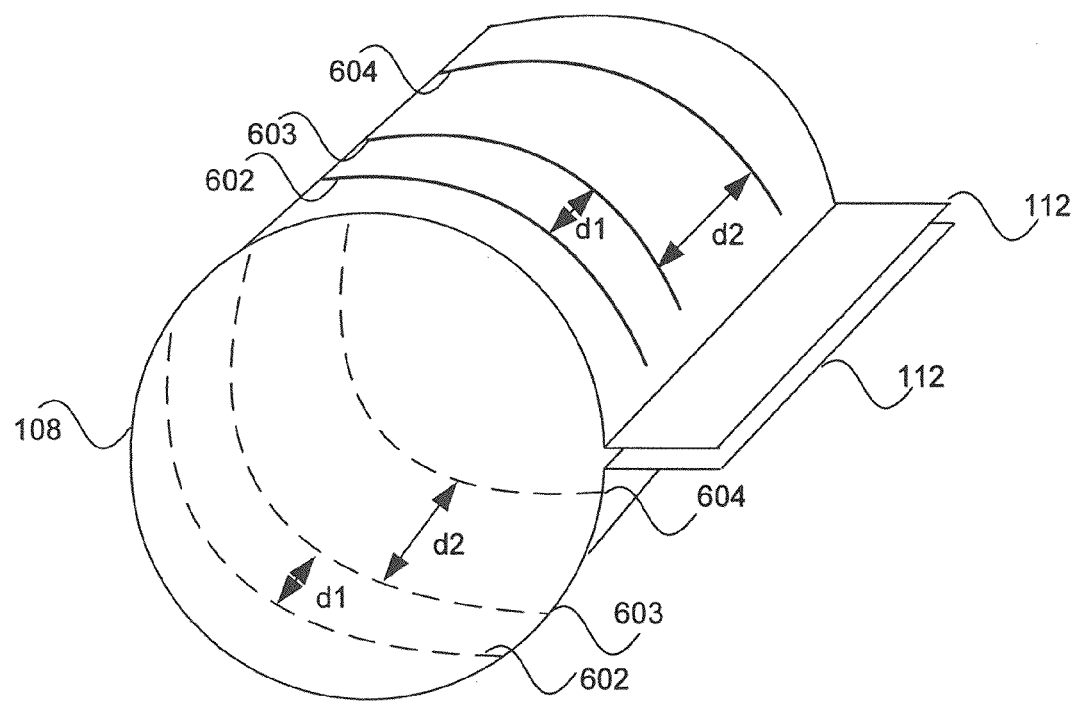
FIG. 6 is a schematic angular view of another embodiment of a cuff showing positioning of electrode contacts.

FIG. 6 is a schematic angular view of another embodiment of a cuff showing positioning of electrode contacts. Shown is a full cuff employing different positioning of electrode contacts 602-604. That is, the distances d1 and d2 between electrode contacts 602-604 are different from each other.

Figure 7:
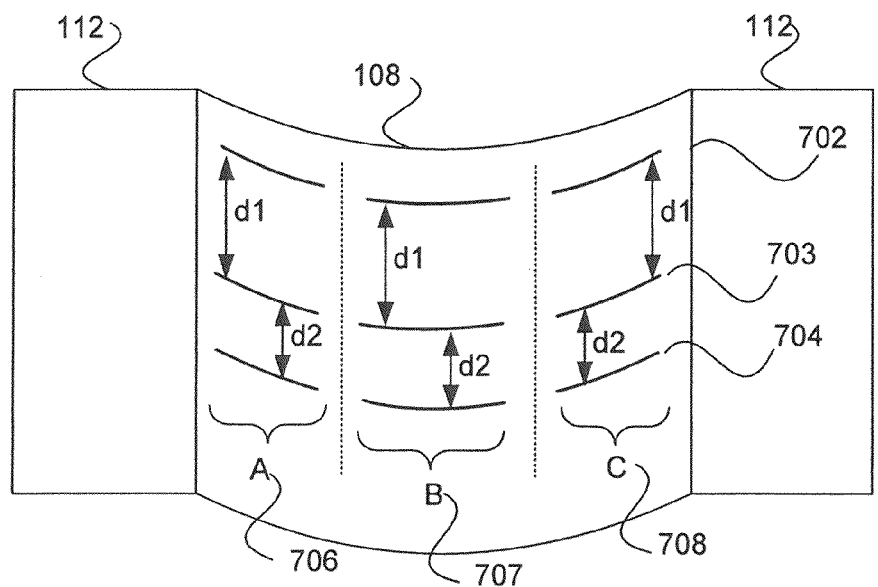
FIG. 7 is a schematic view of another embodiment of a cuff showing a plurality of arrays of electrode contacts with different electrode contact positioning.

FIG. 7 is a schematic view of another embodiment of a cuff showing a plurality of arrays of electrode contacts with different electrode contact positioning. Shown is one embodiment of a saddle electrode contact arrangement with multiple electrode contact arrays 706-708 (A, B, and C) with different positioning of electrode contacts within a given electrode contact array. An arrangement such as illustrated in FIG. 7 may provide spatial selectivity of electrode contacts, and enable a selection of higher current densities than might be achieved with a set of longer electrode contacts. In one embodiment, electrode contact arrays 706-708 (A, B, and C) may be used simultaneously. In another embodiment, electrode contact arrays 706-708 (A, B, and C) may be used on different timing channels. In another embodiment; one or more (e.g., a subset) of the electrode contact arrays may be selected.

In addition, a pre-pulse may be applied at a bipolar distance selected for one depth. In one embodiment, electrical stimulation may be applied with a different bipolar spacing than that used for the pre-pulse stimulation, to affect a different (or even an overlapping) target population. In one embodiment, the pre-pulsing and stimulation may be applied within a same electrode contact array (A, B, or C). In another embodiment, the pre-pulsing and stimulation may be applied within different electrode contact arrays. However, pre-pulsing is not constrained to electrode contact array arrangements, and pre-pulsing may be used for any of the embodiments described herein, without departing from the scope or spirit of the invention. For example, pre-pulsing may be applied for neuromodulation via a plurality of electrode contacts. A pre-pulse may not necessarily stimulate tissue, and may, in some instances, prevent or otherwise reduce stimulation of selected tissue by a subsequent pulse, to allow targeting of other tissues.

Figure 8:
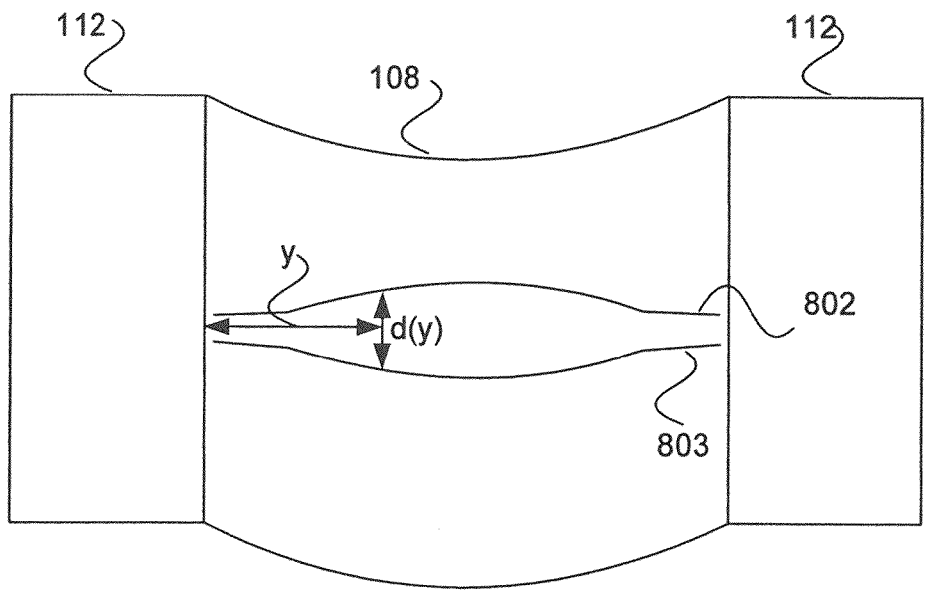
FIG. 8 is a schematic view of an embodiment of a cuff showing varying positioning between electrode contacts.

In other embodiments, the distances between electrode contacts may be variable. For example, in some embodiments, the separation distance between two (or more) electrode contacts may vary along a length of the electrode contacts. As such, FIG. 8 is a schematic view of an embodiment of a cuff showing a varying distance between electrode contacts. Shown in the figure, a distance d(y) between electrode contacts 802 and 803 may vary according to a distance y along the first portion 108 of cuff 102. In one embodiment, the distance y may be measured from a point of intersection between the second portion 112 and the first portion 108 of the cuff. However, the invention is not limited to measuring from this point, and another position may be employed without departing from the scope or spirit of the invention.

As shown in FIG. 8, the electrode contacts 802-803 are separated by a greater distance towards a center of the length of the electrode contacts than at an end of the electrode contacts (nearer to the edge of first portion 108). By changing the distance or separation between electrode contacts based, in part, on a position along the cuff, thresholds may be reduced. In one embodiment, the threshold may be reduced, even if a target stimulation depth changes along a width or length of the cuff. It will be recognized that other electrode contact arrangements with varying distances between the electrode contacts can also be formed. Such arrangements may present the electrode contacts in a regular or irregular pattern.

Figure 9:
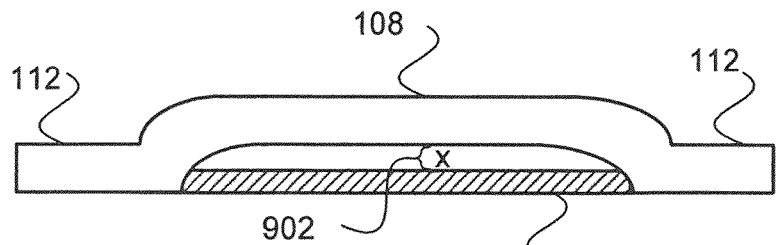
FIG. 9 is a schematic side view of one embodiment of a portion of a cuff showing a distance from a portion of a nerve.

FIG. 9 illustrates a schematic side view of one embodiment of a portion of a cuff showing a distance from a portion of a nerve, where target stimulation depth 902 varies such that a depth along the edges of the first portion 108 of cuff 102 might be less than the target stimulation depth towards the center of the first portion 108 of cuff 102.

Figure 10:
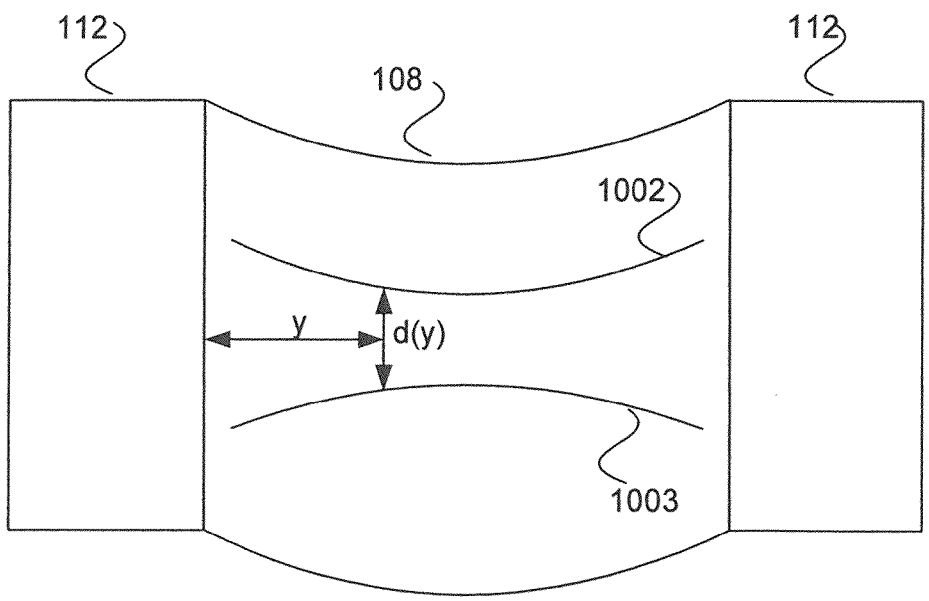
FIG. 10 is a schematic view of another embodiment of a cuff showing varying positioning between electrode contacts.

FIG. 10 is a schematic view of another embodiment of a cuff showing a varying distance between electrode contacts. As shown in the figure, distance d(y) between electrode contacts 1002-1003 is at a lesser distance towards a center of the length of the electrode contacts than at an end of the electrode contacts. This embodiment, enables the distance d(y) to vary based, in part, on a position along an electrode contact (1002-1003) to obtain a threshold profile that may increase uniformity across the nerve or other target fiber. Such uniformity of stimulation threshold across the nerve, nerve bundle, or other fiber, may be employed to minimize over stimulation of nerves.

It should be noted, that while FIGS. 8 and 10 illustrate two electrode contacts with a variable distance between the electrode contacts, the invention is not limited to two electrode contacts. For example, in one embodiment, electrode contact 802 and electrode contact 803 of FIG. 8 may each represent a plurality of electrode contacts. Similarly, electrode contact 1002 and electrode contact 1003 of FIG. 9 may each represent more than one electrode contact. That is, electrode contact 1002 may represent two or more electrode contacts, while electrode contact 1003 may also represent two or more electrode contacts, without departing from the scope or spirit of the invention.

Figure 11:
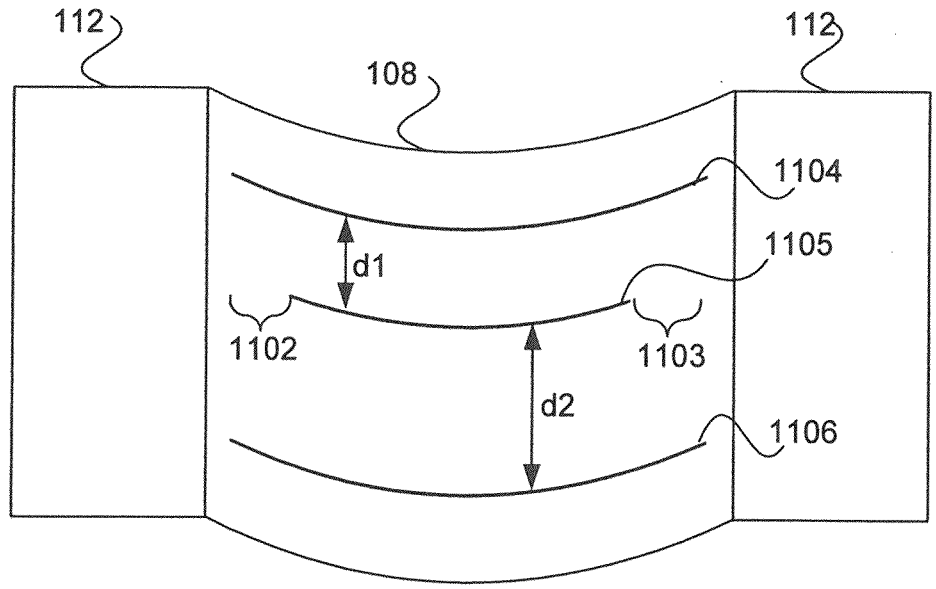
FIG. 11 is a schematic view of another embodiment of a cuff with at least one electrode contact of a different length than each immediately adjacent electrode contact.

FIG. 11 is a schematic view of another embodiment of a cuff with at least one electrode contact having a different length than at least one adjacent electrode contact. As shown in the figure, an inner electrode contact 1105 is of a shorter length (by length segments 1102 and 1103) than at least one adjacent electrode contact 1104 or 1106. In one embodiment, distances d1 and d2 may equal. However, in another embodiment distances d1 and d2 may be different.

The arrangement of FIG. 11 may be employed where a current density and activating mechanism are higher at an endpoint of an electrode contact than towards a center of the electrode contact. In addition, the arrangement shown in FIG. 11 may provide an increased uniformity activation scheme where one or more outer electrode contacts (1104 and/or 1106) are selected to be of one polarity and the inner electrode contact 1105 is selected with an opposite polarity.

Figure 12:
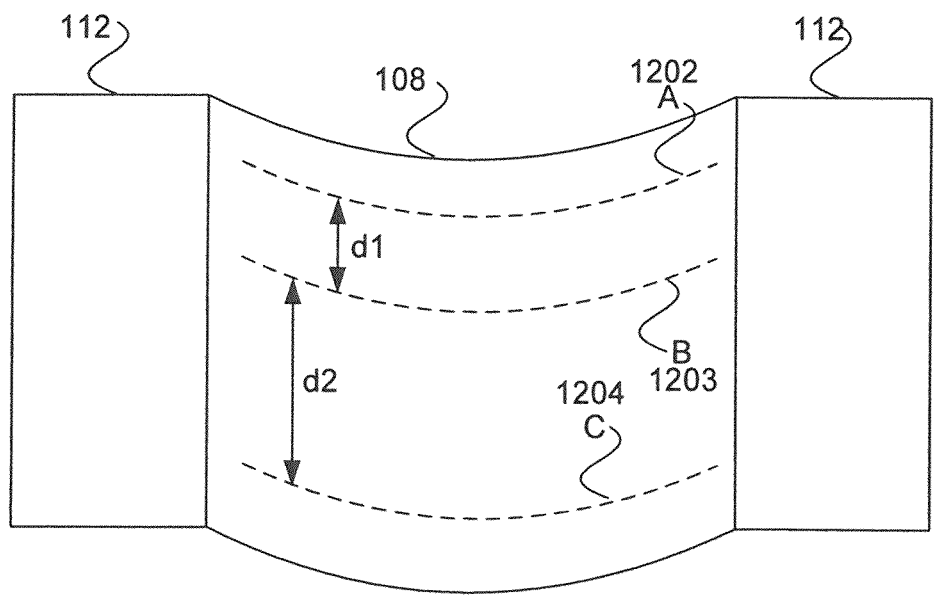
FIG. 12 is a schematic view of an embodiment of a cuff showing groupings of a plurality of electrode contacts.

FIG. 12 is a schematic view of an embodiment of a cuff showing groupings of a plurality of electrode contacts. As shown in the figure, dotted lines 1202-1204 represent three electrode contact groupings, each electrode contact grouping including a plurality of electrode contacts. Distances d1 and d2 between each electrode contact grouping may be selected to be different. Moreover, each electrode contact within an electrode contact grouping may be configured as independent electrode contacts, electrically connected to each other on the cuff, or even electrically connected to each other via electronics within a stimulator unit, such as described below in conjunction with FIG. 13. The concept of splitting electrode contacts, and/or connecting them to each other may also be applied to each of the embodiments described herein. Moreover, in one embodiment, electrical stimulation may be applied across electrode contacts that are lateral to each other, or non-lateral to each other, thereby taking advantage of the variety of differences in distances between lateral and non-lateral electrode contacts within or across the electrode contact groupings.

Figure 13:
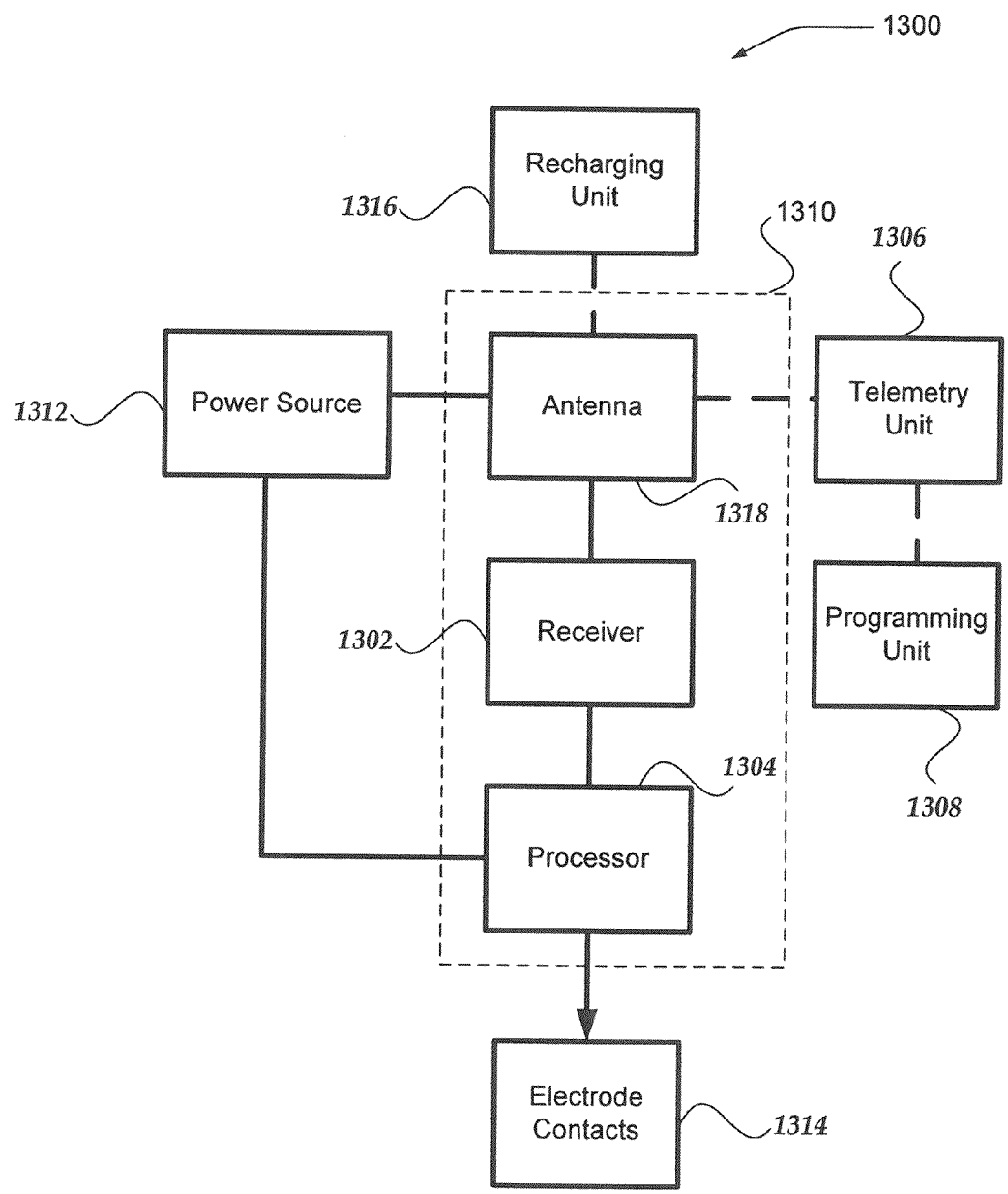
FIG. 13 is a schematic cross-sectional view of one embodiment of a stimulator unit.

FIG. 13 is a schematic overview of one embodiment of components of a stimulation system 1300 including an electronic subassembly 1310 (which may or may not include power source 1312), according to the invention. In one embodiment, electronic subassembly 1310 is referred to as a stimulator unit, or as a portion of a stimulator unit (e.g., a portion of an implantable pulse generator). It will be understood that stimulation system 1300 can include more, fewer, or different components and can have a variety of different configurations including those configurations disclosed in the stimulator references cited herein. Some or all of the components of stimulation system 1300 can be positioned on one or more circuit boards or similar carriers within housing of a stimulator unit if desired. Thus, in one embodiment, a stimulator unit may further include one or more of power source 1312, telemetry unit 1306, programming unit 1308, and/or recharging unit 1316, without departing from the scope or spirit of the invention.

Any power source 1312 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bio-energy power sources, fuel cells, bioelectric cells, osmotic pressure pumps, and the like including the power sources described in U.S. Patent Application Publication No. 2004/0059392, which is incorporated herein by reference.

As another alternative, power can be supplied by an external power source through inductive coupling via an optional antenna 1318 or a secondary antenna (not shown). The external power source can be in a device that is mounted on the skin of the user or in a unit that is provided near the stimulator user on a permanent or periodic basis.

If the power source 1312 is a rechargeable battery, the battery may be recharged using the optional antenna 1318, if desired. Power can be provided to the battery for recharging by inductively coupling the battery through the antenna to a recharging unit 1316 external to the user.

In one embodiment, electrical current is emitted by the electrode contacts 1314 to stimulate motor nerve fibers, muscle fibers, or other body tissues near the electrodes. The electronic subassembly 1310 provides the electronics used to operate the stimulator and generate the electrical pulses at the electrode contacts 1314 to produce stimulation of the body tissues. FIG. 13 illustrates one embodiment of components of the electronic subassembly and associated units.

In the illustrated embodiment, a processor 1304 is generally included in the electronic subassembly 1310 to control the timing and electrical characteristics of the stimulator. For example, the processor can, if desired, control one or more of the timing, frequency, strength, duration, and waveform of the pulses. In addition, the processor 1304 can select which electrode contacts can be used to provide stimulation, if desired. In some embodiments, the processor may select which electrode contact(s) are cathodes and which electrode contact(s) are anodes. In some embodiments, the processor may be used to identify which electrode contacts provide the most useful stimulation of the desired tissue. This process may be performed using an external programming unit that is in communication with the processor 1304.

Any processor can be used and can be as simple as an electronic device that produces pulses at a regular interval or the processor can be capable of receiving and interpreting instructions from an external programming unit 1308 that allow modification of pulse characteristics. In the illustrated embodiment, the processor 1304 is coupled to a receiver 1302 which, in turn, is coupled to the optional antenna 1318. This allows the processor to receive instructions from an external source to direct the pulse characteristics and the selection of electrode contacts, if desired.

In one embodiment, the antenna 1318 is capable of receiving signals (e.g., RF signals) from an external telemetry unit 1306 which may be programmed by a programming unit 1308. The programming unit 1308 can be external to, or part of, the telemetry unit 1306. The telemetry unit 1306 can be a device that is worn on the skin of the user or can be carried by the user and can have a form similar to a pager or cellular phone, if desired. As another alternative, the telemetry unit may not be worn or carried by the user but may only be available at a home station or at a clinician's office. The programming unit 1308 can be any unit that can provide information to the telemetry unit for transmission to the stimulator. The programming unit 1308 can be part of the telemetry unit 1306 or can provide signals or information to the telemetry unit via a wireless or wired connection. One example of a suitable programming unit is a computer operated by the user or clinician to send signals to the telemetry unit.

The signals sent to the processor 1304 via the antenna 1318 and receiver 1302 can be used to modify or otherwise direct the operation of the stimulator. For example, the signals may be used to modify the pulses or pre-pulses of the stimulator such as modifying one or more of pulse duration, pulse frequency, pulse waveform, and pulse strength. The signals may also direct the stimulator to cease operation or to start operation or to start charging the battery. In other embodiments, the electronic subassembly 1310 does not include an antenna 1318 or receiver 1302 and the processor operates as programmed.

Optionally, the stimulator may include a transmitter (not shown) coupled to the processor and antenna for transmitting signals back to the telemetry unit 1306 or another unit capable of receiving the signals. For example, the stimulator may transmit signals indicating whether the stimulator is operating properly or not or indicating when the battery needs to be charged. The processor may also be capable of transmitting information about the pulse characteristics so that a user or clinician can determine or verify the characteristics.

The optional antenna 1318 can have any form. In one embodiment, the antenna comprises a coiled wire that is wrapped at least partially around the electronic subassembly within or on the housing.

Any method of manufacture of the components of the system for stimulation can be used. Particular components such as, the electronic subassembly, power source, and antenna, can be placed inside a housing (or, alternatively, the housing can be formed, e.g., molded, around the components) to form an implantable pulse generator.

A stimulator can be implanted into a patient and electrical signals can be provided to the conductive electrode contact(s) 1314 to stimulate a tissue. In one embodiment, a method of using an implantable stimulator includes implanting an implantable stimulator comprising a conductor. The conductor may comprise electrode contacts 1314 that are disposed at a distal end of the conductor. Electrode contacts 1314 may be arranged as described above. An electrical signal is provided to at least one electrode contacts 1314 to stimulate a tissue. Moreover, an implantable stimulator can be implanted into the body tissue using a variety of methods including surgical methods.

The electrode contacts 1314 may be selectively stimulated. Electrical signals may be provided to the electrode contacts 1314 of the stimulator simultaneously. Alternatively, electrical signals can be provided to the electrode contacts 1314 of the stimulator independently of one another. Coordination of the electrical signals provided to the electrode contact (s) 1314 is often facilitated by a processor 1304.

The stimulation system 1300 may be used to provide various electrical signals to the electrode contacts 1314 arranged on the cuff to stimulate the nerve, or other fiber, including, but not limited to pre-pulsing stimulations, or other waveform stimulations. In one embodiment, the electrical signals may be applied to provide a hybrid of depth stimulations. In another embodiment, the electrical signals may be applied on different timing channels to the electrode contacts.

Figure 14:
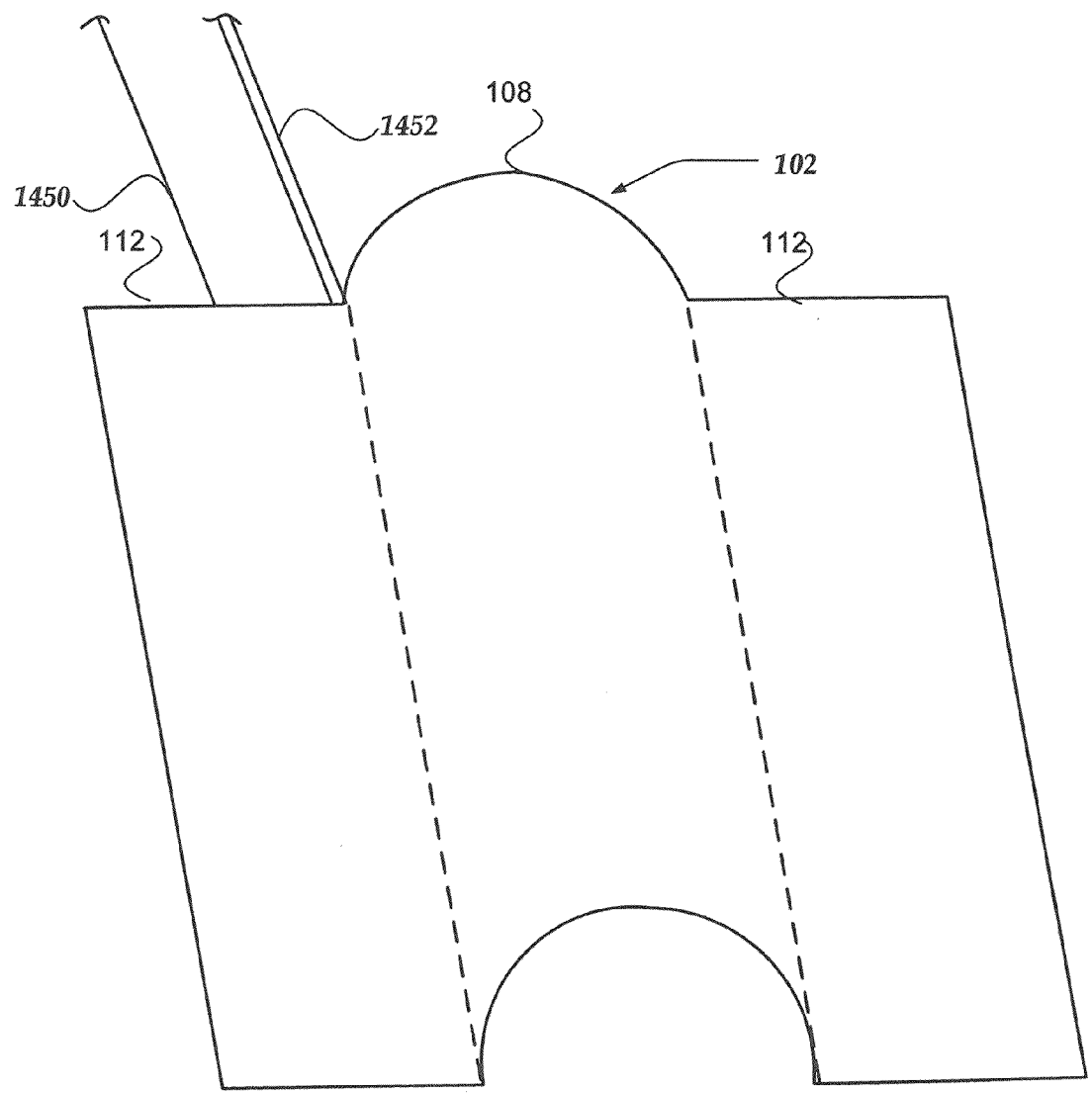
FIG. 14 is a perspective view of one embodiment of a cuff for use in a stimulation system, according to the invention.

FIG. 14 is a perspective view of one embodiment of a cuff for use in a stimulator device. As shown in the figure, cuff 102 is coupled to conductor 1450 and further optionally includes one or more lumens 1452 entering the cuff with corresponding opening(s) through which a drug can be infused to the nerve or adjacent tissue. In one embodiment, conductor 1450 includes a surrounding insulation material.

The lumens 1452 can connect through or along side of the conductor 1450 to the stimulator unit or a separate drug infusion unit that contains a reservoir of the drug and a pump that can provide the drug on a continuous, regular, irregular, or "as needed" basis. A processor may be provided to control the pump. The processor is optionally programmable from an external source by transmitting signals to the drug infusion processor. As an alternative, the lumen(s) 1452 can be accessed externally to infuse the drug using a drug infusion unit that is positioned on the skin of the patient or elsewhere or the lumen can be accessed to provide periodic infusions using a needle or the like.

Optionally, the cuff 102 can also include one or more electrode contacts or sensors that are used to detect or measure the state of the nerve, the state of the erectile dysfunction or other disorder, or the state of the patient. These electrode contacts or sensors can be observed by the stimulator unit or a separate control unit.

An implantable stimulator may include an implantable stimulator unit (such as an implantable pulse generator), a cuff that is disposed around or near the nerve and contains electrode contacts, and a conductor coupling the implantable stimulator unit to the electrode contacts on the cuff.

The above specification, examples, and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A stimulation system for a nerve, comprising:
   a cuff configured and arranged to be placed, at least partially, around the nerve;
   a plurality of electrode contacts disposed on the cuff, the plurality of electrode contacts comprising a first electrode contact, a second electrode contact adjacent the first electrode contact, a third electrode contact adjacent the second electrode contact, and a fourth electrode contact adjacent the third electrode contact, such that 1) a distance between the first electrode contact and the second electrode contact, 2) a distance between the second electrode contact and the third electrode contact, and 3) a distance between the third electrode contact and the fourth electrode contact are all different from each other; and a stimulator unit electrically coupled to the plurality of electrode contacts and configured and arranged for selecting two of the plurality of electrode contacts and providing stimulation to adjacent tissue using the two of the plurality of electrode contacts.

2. The stimulation system of claim 1, wherein the distances between the first, second, third, and fourth electrode contacts are selected, based in part, on another distance, the other distance being between the nerve and a point on the first electrode contact.

3. The stimulation system of claim 1, wherein, electrode contacts within the plurality of electrode contacts are arranged within a plurality of electrode contact arrays along the cuff, wherein the distances between one electrode contact array and each electrode contact array immediately adjacent to the one electrode contact array are different.

4. The stimulation system of claim 1, wherein the first electrode contact within the plurality of electrode contacts has a shorter length than at least one of the electrode contacts immediately adjacent to the first electrode contact.

5. The stimulation system of claim 1, the stimulator unit is arranged to provide a pre-pulse prior to providing electrical signals for stimulation of a nerve via the plurality of electrode contacts, wherein the pre-pulse does not stimulate the nerve.

6. The stimulation system of claim 1, wherein the cuff comprises a first portion that is curved and a second portion that is flat and attached to the first portion, wherein the cuff is configured and arranged so that both the first and second portions are disposed around the nerve.

7. The stimulation system of claim 6, wherein the curved portion has a shape of a half cylinder.

8. The stimulation system of claim 6, further comprising a third portion that is flat and attached to the first portion, wherein the second portion extends from a first end of the first portion and the third portion extends from a second end of the first portion, wherein the second end is opposite the first end.

9. The stimulation system of claim 6, wherein the second portion extends below the first portion.

10. A stimulation system for a nerve, comprising:
a cuff configured and arranged to be placed, at least partially, around the nerve;
a plurality of electrode contacts disposed on the cuff such that distances between a first electrode contact within the plurality of electrode contacts and each electrode contact immediately adjacent to the first electrode contact are different; and
a stimulator unit electrically coupled to the plurality of electrode contacts and configured and arranged for selecting two of the plurality of elements and providing stimulation to adjacent tissue using the two of the plurality of electrodes, wherein the plurality of electrode contacts further comprises at least two groupings of electrode contacts within the plurality of electrode contacts, wherein distances between one electrode contact within one of the at least two groupings and each electrode contact immediately adjacent to the one electrode contact within the same grouping are different.

11. The stimulation system of claim 10, wherein each electrode contact within one of the at least two groupings of electrode contacts is configured to operate independent of another electrode contact within the same grouping.

12. The stimulation system of claim 10, wherein each electrode contact within one of the at least two groupings of electrode contacts is configured to be electrically coupled together with each electrode contact within the same grouping to operate collectively.

13. A method of stimulating a nerve, the method comprising:
disposing a cuff, at least partially, around the nerve, the cuff having a plurality of electrode contacts disposed on the cuff such that a distance between a first electrode contact within the plurality of electrode contacts and at least one electrode contact immediately adjacent to the first electrode contact varies along a length of the first electrode contact;
coupling the cuff to a stimulator unit; and
providing electrical signals from the stimulator unit to a pair of the electrode contacts of the cuff to stimulate the nerve.

14. The method of claim 13, wherein, the nerve is a vagus nerve and disposing the cuff around the nerve comprises disposing the cuff around the vagus nerve.

15. The method of claim 13, wherein the nerve comprises a cavernous nerve and disposing the cuff around the nerve comprises disposing the cuff around a neurovascular bundle comprising the cavernous nerve.

16. The method of claim 15, wherein the cuff comprises a first portion that is curved and a second portion that is flat and wherein disposing the cuff, at least partially, around the nerve comprises disposing the cuff around the cavernous nerve with the second portion disposed between the cavernous nerve and a rectum.

17. The method of claim 13, further comprising providing a pre-pulse prior to providing the electrode signals to the electrode contacts to stimulate the nerve, wherein the pre-pulse does not stimulate the nerve.

18. The method of claim 13, wherein the cuff comprises a first portion that is curved and a second portion that is flat and wherein disposing the cuff, at least partially, around the nerve comprises disposing the first portion of the cuff over a region of the nerve and disposing the second portion of the cuff beneath the region of the nerve.

19. The method of claim 18, wherein the cuff comprises a third portion that is curved and wherein disposing the cuff, at least partially, around the nerve comprises disposing the third portion of the cuff beneath the region of the nerve.

* * * * *